(12) United States Patent
Bush et al.

(10) Patent No.: US 6,610,706 B1
(45) Date of Patent: Aug. 26, 2003

(54) CRYSTALLINE FORM OF 6-HYDROXY-3-(4-[2-(PIPERIDIN-1-YL)ETHOXY]PHENOXY)-2-(4-METHOXYPHENYL)BENZO[B]THIOPHENE HYDROCHLORIDE

(75) Inventors: Julie Kay Bush, Fishers, IN (US); Preston Charles Conrad, Indianapolis, IN (US); Merlyn Gerard Flom, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/031,324

(22) PCT Filed: Jul. 17, 2000

(86) PCT No.: PCT/US00/16332
§ 371 (c)(1), (2), (4) Date: Jan. 10, 2002

(87) PCT Pub. No.: WO01/09115
PCT Pub. Date: Feb. 8, 2001

Related U.S. Application Data

(60) Provisional application No. 60/149,820, filed on Aug. 19, 1999, provisional application No. 60/147,642, filed on Aug. 6, 1999, and provisional application No. 60/146,184, filed on Jul. 29, 1999.

(51) Int. Cl.[7] .................... A61K 31/445; C07D 409/12
(52) U.S. Cl. ........................ 514/324; 546/202
(58) Field of Search ............................ 514/324; 546/202

(56) References Cited

U.S. PATENT DOCUMENTS

| | | | |
|---|---|---|---|
| 5,510,357 A | 4/1996 | Palkowitz | 514/324 |
| 5,723,474 A | 3/1998 | Palkowitz | 514/324 |
| 5,856,339 A | 1/1999 | Palkowitz | 514/324 |
| 5,856,340 A | 1/1999 | Palkowitz | 514/324 |
| 5,919,800 A | 7/1999 | Palkowitz | 514/324 |
| 5,977,093 A | 11/1999 | Palkowitz | 514/171 |
| 5,998,441 A | 12/1999 | Palkowitz | 514/324 |
| 6,077,852 A | 6/2000 | Bales | 514/319 |
| 6,288,108 B1 * | 9/2001 | Bryant et al. | 514/443 |
| 2002/0013342 A1 * | 1/2002 | Bales et al. | 514/319 |

FOREIGN PATENT DOCUMENTS

| | | |
|---|---|---|
| WO | WO 9845286 | 10/1998 |
| WO | WO 9845288 | 10/1998 |
| WO | WO 2001085147 | 11/2001 |

OTHER PUBLICATIONS

Drugs Future, 24(6):599–604, 1999.

* cited by examiner

*Primary Examiner*—Ceila Chang
(74) *Attorney, Agent, or Firm*—Gilbert T. Voy

(57) ABSTRACT

The present invention is directed to a novel crystalline hydrate of 6-hydroxy-3-(4-[2-(piperidin-1-yl)ethoxy]-phenoxy)-2-(4-methoxyphenyl)benzo[b]thiophene hydrochloride and uses for same, including inhibition of disease states associated with estrogen deprivation including cardiovascular disease, hyperlipidemia, and osteoporosis; and inhibition of other pathological conditions such as endometriosis, uterine fibrosis, estrogen-dependent cancer (including breast and uterine cancer), prostate cancer, benign prostatic hyperplasia, CNS disorders including Alzheimer's disease, prevention of breast cancer, and up-regulating ChAT.

4 Claims, 5 Drawing Sheets

CRYSTALLINE FORM OF 6-HYDROXY-3-(4-[2-(PIPERIDIN-1-YL)ETHOXY]PHENOXY)-2-(4-METHOXYPHENYL)BENZO[B]THIOPHENE HYDROCHLORIDE

This application claims the benefit under Title 35, U.S.C. §120 of PCT International Patent Application No. PCT/US00/16332, filed Jul. 17, 2000, which claims priority under Title 35 U.S.C. §119(e) of Application Nos. 60/146,184, filed Jul. 29, 1999; 60/147,642, filed Aug. 6, 1999; and 60/149,820 filed Aug. 19, 1999.

BACKGROUND OF THE INVENTION

6-Hydroxy-3-(4-[2-(piperidin-1-yl)ethoxy]phenoxy)-2-(4-methoxyphenyl)benzo[b]thiophene hydrochloride (arzoxifene) was first described generically in U.S. Pat. No. 5,510,357 and was specifically disclosed in U.S. Pat. No. 5,723,474 ('474) and European Patent Application 0729956. Arzoxifene is a nonsteroidal mixed estrogen antagonist/agonist, useful for, inter alia, lowering serum cholesterol and for inhibiting hyperlipidemia, osteoporosis, estrogen dependent cancers including breast and uterine cancer, endometriosis, CNS disorders including Alzheimer's disease, aortal smooth muscle cell proliferation, and restenosis.

Specifically, arzoxifene is useful for, and is being clinically evaluated for the treatment of receptor positive metastatic breast cancer; the adjuvent treatment of receptor positive patients following appropriate systemic or local therapy; the reduction of recurrence of invasive and noninvasive breast cancer; and the reduction of the incidence of invasive breast cancer and ductal carcinoma in situ (DCIS). Arzoxifene is also useful in combination with radiotherapy, aromatase inhibitors, LHRH analogues, and acetyl choline esterase (AChE) inhibitors.

X-ray powder diffraction (XRD), thermogravimetric (TGA), proton nuclear magnetic resonance ($^1$H NMR) and Karl Fischer (KF) analyses of bulk arzoxifene isolated by the procedures taught in '474 later indicated that said material was hydrated, poorly crystalline, and contained variable amounts of an organic volatile (ethyl acetate) in its lattice.

Poorly crystalline materials are typically less desirable than highly crystalline materials for formulation processing. In addition, it is generally not desirable to formulate pharmaceuticals containing substantial amounts of organic solvent (e.g., ethyl acetate) due to potential solvent toxicity to the recipient thereof and changes in potency of the pharmaceutical as a function of the solvent.

Although the arzoxifene prepared by the procedures taught in '474 could be used as a pharmaceutical it would be highly desired and advantageous to find a more crystalline form of arzoxifene that did not contain an organic solvent within its crystal lattice which could be reproducibly and efficiently prepared on a commercial scale.

SUMMARY OF THE INVENTION

The present invention is related to a novel non-stoichiometric hydrated crystalline form of 6-hydroxy-3-(4-[2-(piperidin-1-yl)ethoxy]phenoxy)-2-(4-methoxyphenyl)benzo[b]thiophene hydrochloride (F-III) having an X-ray diffraction pattern which comprises the following peaks: 4.6±0.2, 7.8±0.2, 9.3±0.2, 14.0±0.2, 17.6±0.2, 20.8±0.2, and 24.3±0.2° in 2θ; when obtained at 25±2° C. and 35±10% relative humidity (RH) from a copper radiation source.

Moreover the present invention relates to a pharmaceutical formulation comprising F-III; one or more pharmaceutical carriers, diluents, or excipients; and optionally estrogen, optionally progestin, optionally an aromatase inhibitor, optionally an LHRH analogue and optionally an acetyl choline esterase (AChE) inhibitor.

In addition, the present invention is related to methods for using F-III to inhibit pathological conditions such as: uterine fibrosis, endometriosis, aortal smooth muscle cell proliferation, restenosis, breast cancer, uterine cancer, prostatic cancer, benign prostatic hyperplasia, bone loss, osteoporosis, cardiovascular disease, hyperlipidemia, CNS disorders, and Alzheimer's disease and for using F-III for the manufacture of a medicament for inhibiting same.

The present invention is further related to methods for using F-III to up-regulate choline acetyltransferase (ChAT) and for using F-III for the manufacture of a medicament for up-regulating same.

DETAILED DESCRIPTION OF THE INVENTION

Figure 1:
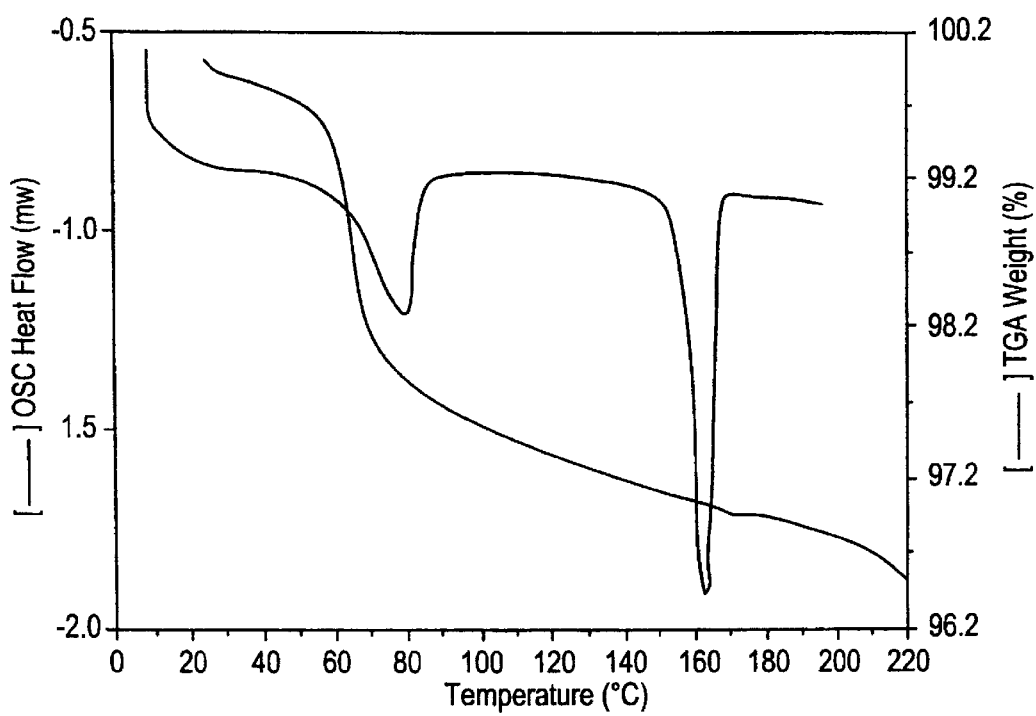
FIG. 1 is a representative differential scanning calorimetry (DSC)/TGA trace of S-II.

Bulk arzoxifene prepared by the procedure taught in '474 (Example 41, crystallization from a mixture of ethanol and ethyl acetate, filtration and drying of the filter cake in vacuo to a constant weight at room temperature) was characterized by XRD and was found to be poorly crystalline. $^1$H NMR confirmed that the bulk material contained 6% ethyl acetate.

The crystallization procedure taught in '474 was subsequently modified so that ethanol was added to a suspension of crude arzoxifene in refluxing ethyl acetate. Upon cooling and vacuum filtration, the solid that results from this modified procedure is a highly crystalline mixed ethyl acetate/water solvate of arzoxifene (hereinafter referred to as S-II) which was later discovered to be a starting material for F-I (another non-stoichiometric hydrated crystalline form of arzoxifene).

F-I may be prepared by removing the ethyl acetate from S-II's crystal lattice by vacuum drying/annealing S-II at elevated temperatures. The time and temperature required to anneal S-II in order to prepare F-I will vary from lot to lot but is typically on the order of 5 days at around 100° C. High temperatures are needed to effect the conversion of S-II to F-I via this procedure, since slurrying S-II in water at ambient temperature or storing a sample at 98% RH for 3 weeks afforded no conversion to F-I. Furthermore, drying S-II in a convection oven at high temperatures did not desolvate the material either, suggesting that a vacuum is also required to pull the ethyl acetate from S-II's lattice. Preferably, F-I is readily prepared and isolated at ambient temperature by crystallization of arzoxifene (or any polymorph/solvate thereof) from tetrahydrofuran.

In accordance with the present invention, a particularly preferred form of arzoxifene is F-III. F-III is readily prepared and isolated at ambient temperature. Only moderate drying conditions are required to remove low levels of residual crystallization solvent in the preparation of F-III. These moderate drying conditions consistently result in a solid of high purity (i.e., free of residual organic solvent) and crystallinity and, thus, use of F-III eliminates toxicology issues associated with residual and crystal lattice organic solvent. Furthermore, preparation of F-III is simple and efficient, i.e., is amenable to bulk manufacture.

F-III is readily prepared and isolated at ambient temperature by crystallization of arzoxifene (or any polymorph/solvate thereof) from a mixture of isopropyl alcohol (IPA) and water. Typically, arzoxifene may be suspended in a mixture of IPA and water and heated in order to effect dissolution of the arzoxifene starting material. Once dissolution is achieved, the solution is allowed to cool slowly to room temperature and then further (with the aid of an ice bath or refrigeration) to between 0 and 5° C. After a sufficient amount of time has elapsed for crystallization to occur, the crystals may be collected by vacuum filtration and dried to a constant weight in vacuo to obtain F-III in yields greater than 80%.

Suitable arzoxifene starting material for the above crystallization includes, but is not limited to, S-II, F-I, arzoxifene prepared by the procedures taught in '474, or any mixture thereof. It is not important which form of arzoxifene one starts with because crystallization from IPA and water, according to the procedures described herein, results in F-III crystals. The ratio of water to IPA (v:v) is generally about 1:1 to 9:1. More preferably, the ratio is between 2.5 and 5.6:1. Most preferably, the ratio is between 3 to 5.6:1. Upon collection of the crystals by vacuum filtration, the F-III wet cake may be washed with cold deionized water before drying in vacuo. In addition, slightly elevated drying temperatures (about 50° C. for 12 to 24 hours) are preferred. For commercial scale synthesis of F-III, it may be advantageous to seed the crystallization with F-III.

In a preferred process, F-III is prepared, isolated, and purified contiguous with the chemical removal of the 6-isopropyl hydroxy protecting group from 6-isopropoxy-3-(4-[2-(piperidin-1-yl)ethoxy]phenoxy)-2-(4-methoxyphenyl)benzo[b]thiophene hydrochloride (precursor A). The deprotection reaction is monitored for complete removal of the isopropyl protecting group and once it is determined that the removal is substantially complete, the work-up of the reaction will preferably include a crystallization under the conditions that provide F-III as discussed above and below. Methods for preparing precursor A and for removing the isopropyl group may be found in U.S. Pat. No. 5,723,474, the teachings of which are herein incorporated by reference.

In another preferred process, F-III is prepared, isolated and purified contiguous with the chemical reduction of the S-oxide and chemical removal of the benzyl protecting group from the 6-hydroxyl in 6-benzyloxy-3-(4-[2-(piperidin-1-yl)ethoxy]phenoxy)-2-(4-methoxyphenyl)benzo[b]thiophene-(S-oxide) (precursor B). The reduction and deprotection reactions are monitored for complete reduction of the sulfoxide to the sulfide and complete removal of the benzyl hydroxy protecting group. Once it is determined that the reduction/removal is substantially complete, the work-up of the reaction will preferably include a crystallization under the conditions that provide F-III as discussed herein. Methods for preparing precursor B, for removing the benzyl group, and for reducing the 1-sulfoxide to the corresponding sulfide may also be found in the previously incorporated by reference U.S. Pat. No. 5,723,474.

Irrespective of the chemistry utilized in the deprotection and reduction steps, crystallization of arzoxifene from the IPA/water solutions disclosed herein consistently produces F-III crystals in high purity.

Characterization and Differentiation of S-II, F-I and F-III

DSC/TGA and XRD methods were used to characterize S-II, F-I and F-III. TGA is often very useful for distinguishing between different solid forms of a material because the temperature(s) at which a physical change in a material occurs is usually characteristic of the polymorph or solvate. DSC is a technique that is often used to screen compounds for polymorphism and solvate formation. Lastly, XRD is a technique that detects long-range order in a crystalline material.

Arzoxifene prepared by the procedures taught in '474 gave XRD patterns with poor signal-to-noise ratios and a raised baseline, indicative of poorly crystalline material. Therefore, comparisons of F-I and F-III are made to the material (S-II) produced by the modified arzoxifene crystallization procedure discussed above (addition of ethanol to a suspension of arzoxifene in refluxing ethyl acetate).

Figure 2:
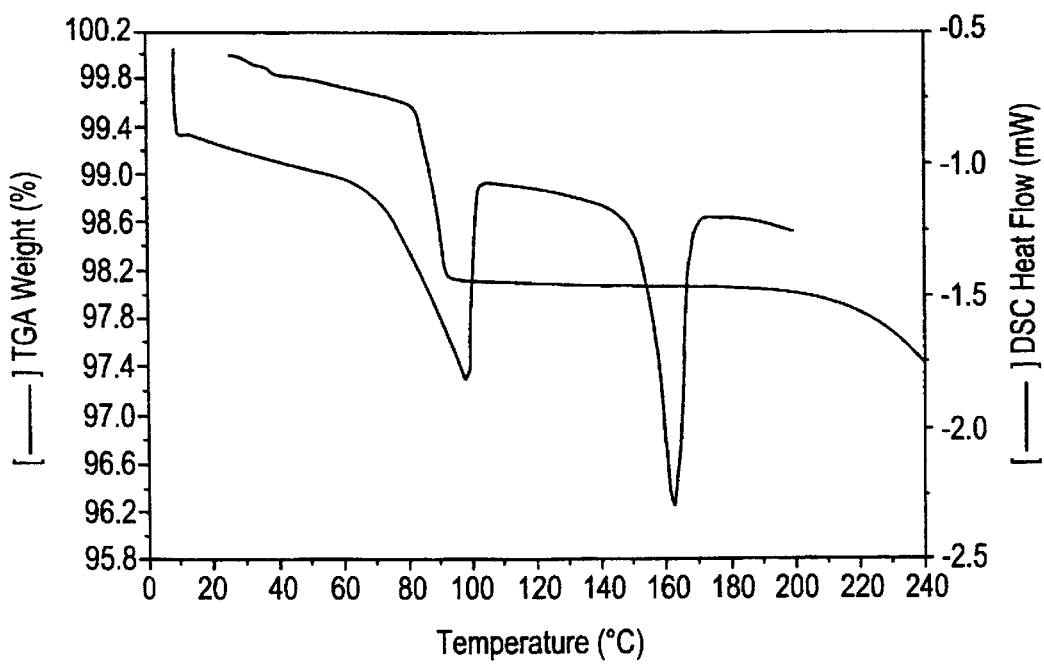
FIG. 2 is a representative DSC/TGA trace of F-I.
Figure 3:
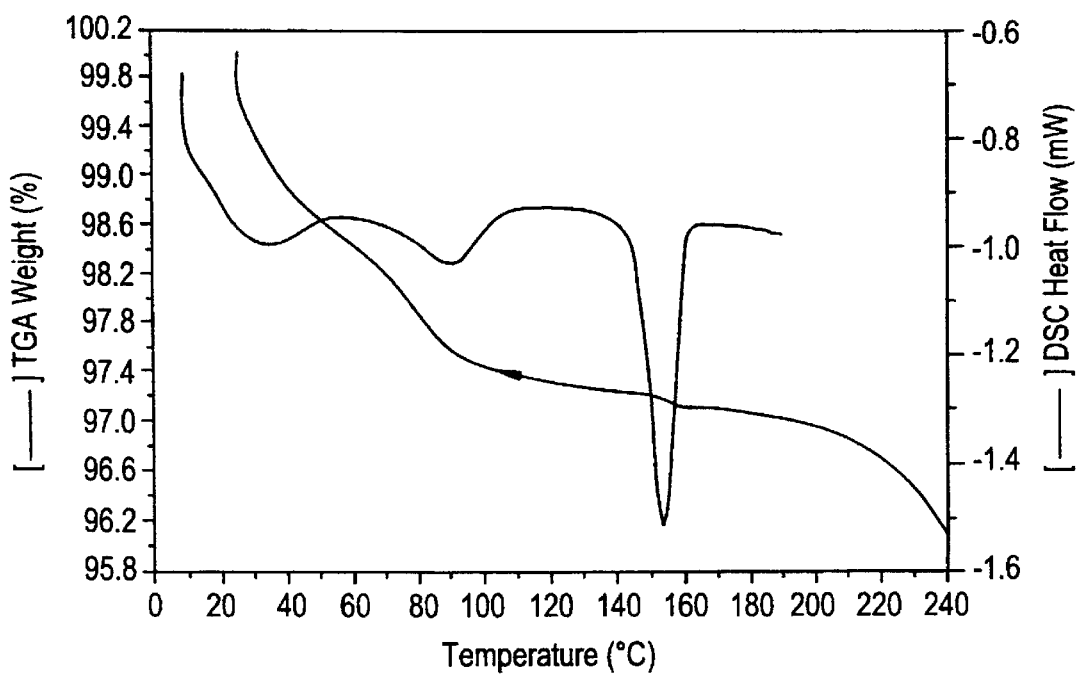
FIG. 3 is a representative DSC/TGA trace of F-III.

Representative DSC/TGA traces of S-II, F-I and F-III are shown in FIGS. 1, 2 and 3, respectively. The DSC trace for S-II shows a broad endotherm beginning at about 62° C., corresponding to the loss of ethyl acetate and water from the lattice. The endotherm beginning at about 152° C. represents a melt. The TGA weight loss of approximately 2.5% occurs simultaneous with the first transition, while the remaining 0.5% weight loss occurs up to the onset of melting, suggesting that some solvent molecules are more tightly held in the lattice.

The DSC trace of F-I shows a broad endotherm beginning at about 75° C., followed by a second endotherm beginning at about 155° C. corresponding to a melt. The TGA trace of F-I shows a gradual weight loss of 0.3% followed by a sharp loss of 1.5%, which together represent dehydration of the lattice. The onset of the first DSC transition and the corresponding TGA weight loss are offset slightly due to the difference in heating rates. The initial weight loss represents weakly held waters of hydration while the second weight loss is consistent with approximately 0.5 mole of water present in the lattice at very low relative humidities (below 5%—see moisture sorption data).

The DSC trace of F-III features a broad, low temperature endotherm at about 30° C., followed by a second broad and relatively weak endotherm beginning at about 70° C., and a final transition beginning at about 146° C. corresponding to a melt. The sharp 1.5% (~0.5 mole) weight loss in the TGA coincident with the first endotherm corresponds to loss of weakly held water molecules, while the additional ~1.6% weight loss above 60° C. represents loss of more tightly held water molecules, i.e., those which are present at very low relative humidities. The weight loss observed after 170° C. corresponds to decomposition of F-III.

The XRD patterns of F-I and F-III feature sharp peaks and a flat baseline, indicative of highly crystalline materials. The angular peak positions in 2θ and corresponding $I/I_o$ data for representative samples of F-I, F-III and S-II is tabulated in Table 1. Although many of the intense reflections are generally at similar diffraction angles, each of the forms gives a different powder pattern, allowing for a clear distinction between S-II, F-I and F-III.

It is well known in the crystallography art that, for any given polymorph, the relative intensities of the diffraction peaks may vary due to preferred orientation resulting from factors such as crystal morphology. Where the effects of preferred orientation are present, peak intensities are altered, but the characteristic peak positions of the polymorph are unchanged. See, e.g., The United States Pharmacopeia #23, National Formulary #18, pages 1843–1844, 1995. Thus, based on peak intensities as well as peak position, F-III may be identified by the presence of peaks at 4.6±0.2, 7.8±0.2, 9.3±0.2, 14.0±0.2, 17.6±0.2, 20.8±0.2, and 24.3±0.2° in 2θ; when the pattern is obtained at 25±2° C. and 35±10% relative humidity from a copper radiation source.

TABLE 1

| S-II | | F-I | | F-III | |
|---|---|---|---|---|---|
| 2θ (°) | I/I$_o$ (%) | 2θ (°) | I/I$_o$ (%) | 2θ (°) | I/I$_o$ (%) |
| 4.67 | 1.3 | 4.92 | 2.6 | 4.63 | 20.8 |
| 5.03 | 6 | 7.69 | 34.6 | 7.82 | 100 |
| 6.83 | 5.8 | 7.91 | 100 | 9.29 | 16.9 |
| 7.17 | 16.1 | 9.89 | 2.5 | 10.16 | 22.7 |
| 7.73 | 100 | 10.22 | 2 | 10.35 | 5.4 |
| 9.03 | 1.3 | 10.74 | 7.4 | 13.77 | 10.7 |
| 9.31 | 1.7 | 14.86 | 9.1 | 13.97 | 15.2 |
| 9.66 | 2.4 | 15.45 | 2.3 | 15.06 | 6.9 |
| 10.27 | 1.6 | 15.92 | 15.9 | 15.71 | 22.3 |
| 10.47 | 2.2 | 16.67 | 1.7 | 15.87 | 7.4 |
| 10.91 | 6.3 | 16.98 | 3.1 | 16.35 | 34.5 |
| 13.63 | 2.1 | 18.28 | 17.8 | 16.77 | 12.3 |
| 14.09 | 4.6 | 18.56 | 7 | 17.28 | 10 |
| 15.10 | 4.1 | 20.58 | 13.1 | 17.62 | 47.9 |
| 15.52 | 10.5 | 20.85 | 8.8 | 18.09 | 43.9 |
| 16.45 | 9.1 | 21.64 | 3.9 | 20.43 | 42 |
| 16.67 | 7.6 | 22.19 | 4.8 | 20.80 | 33.6 |
| 17.21 | 4.9 | 22.65 | 2.9 | 21.31 | 42.7 |
| 17.53 | 2.4 | 23.28 | 3.4 | 21.71 | 13 |
| 18.33 | 28.2 | 23.97 | 11.8 | 21.85 | 14.5 |
| 18.69 | 11.1 | 24.31 | 6.3 | 22.13 | 12.8 |
| 19.37 | 3.5 | 25.52 | 3.9 | 22.26 | 16.3 |
| 20.29 | 8.6 | 26.20 | 3.4 | 23.51 | 13.2 |
| 20.64 | 17.2 | 26.47 | 3.1 | 23.69 | 15.9 |
| 21.02 | 12.7 | 28.84 | 6.4 | 23.91 | 25.6 |
| 21.68 | 5.1 | 30.13 | 3.5 | 24.31 | 38.7 |
| 22.01 | 8.3 | 31.12 | 2.9 | 25.22 | 8 |
| 22.29 | 8 | | | 25.67 | 8.9 |
| 23.17 | 7.8 | | | 27.05 | 18.9 |
| 23.39 | 9.1 | | | 27.89 | 13.3 |
| 24.30 | 13.6 | | | 28.24 | 8.6 |
| 25.76 | 3.4 | | | 28.71 | 21.3 |
| 26.05 | 4 | | | 29.89 | 8.9 |
| 26.63 | 5.5 | | | 30.24 | 18.7 |
| 27.01 | 3.1 | | | 30.88 | 5.8 |
| 27.49 | 2.8 | | | 31.44 | 7.6 |
| 28.10 | 1.8 | | | 33.06 | 4.5 |
| 28.73 | 10.9 | | | 34.36 | 6 |
| 29.42 | 3.2 | | | | |
| 30.00 | 3.7 | | | | |
| 30.89 | 2.1 | | | | |
| 31.34 | 2.4 | | | | |
| 31.70 | 1.1 | | | | |
| 32.81 | 1 | | | | |
| 32.91 | 0.8 | | | | |
| 33.48 | 2 | | | | |

Further Characterization of F-I and F-III

Figure 4:
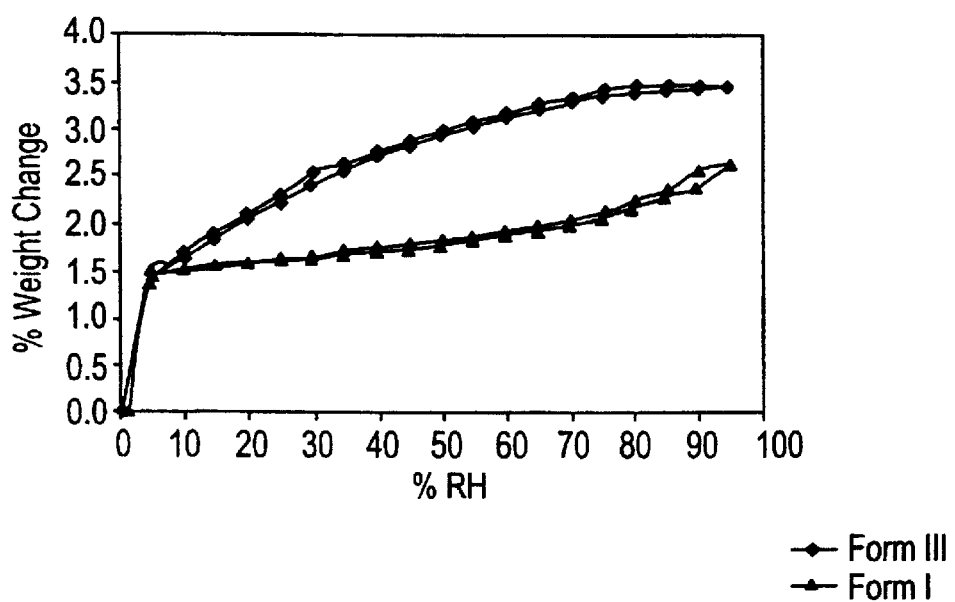
FIG. 4 depicts moisture sorption isotherms for F-I and F-III.

Hygroscopicicity studies were performed on F-I and F-III. The moisture sorption isotherms for F-I and F-III are shown in FIG. 4. Upon initial exposure of the samples to approximately 5% RH, there was an immediate weight gain of 1.5% and 1.7% moisture for F-I and F-III, respectively, equivalent to approximately 0.5 mole of water. Both forms show a continuous sorption of moisture through the entire humidity range, which is likely due to incorporation of water molecules in the lattices.

The difference in the moisture uptake of the two forms likely reflects the amount of water that can be incorporated into the two lattices (i.e., the amount of available space in the lattice that can accommodate water molecules). Lack of hysteresis in the sorption-desorption isotherms of F-I and F-III indicates that the crystal forms rapidly equilibrate at any given humidity.

The moisture sorption profiles for F-I and F-III reveal that these forms are essentially non-stoichiometric hydrates. At ambient relative humidity (about 50% RH), F-I contains approximately 1.7% water, corresponding to 0.5 moles of water, while F-III has sorbed about 3.0% water which corresponds to about 0.85 moles of water. The bulk forms of F-I and F-III rapidly equilibrate with the atmosphere, so that the water content observed by analytical techniques is a reflection of the relative humidity at the time of data collection. Lot-to-lot differences observed in the DSC data likely results from the samples being hydrated to different extents due to different ambient storage conditions.

XRD patterns were obtained for samples of F-I and F-III stored at different relative humidities (0, 22, 50, and 80%). There is a gradual shifting of the initial (0% RH) F-III peaks at about 13.8, 17.6, 18.0, 20.5 and 24.0° in 2θ as well as slight shifting of less intense peaks, as the relative humidity is increased. These observed changes in the XRD patterns of F-III indicate that the unit cell dimensions are changing, presumably to accommodate weakly held water molecules as the relative humidity is increased. The continuous shifting of peaks with humidity correlates well with moisture sorption data that showed a gradual weight gain over this RH range, providing evidence for variable hydrate formation.

A similar experiment was carried out on F-I to determine whether varying the relative humidity would have a similar effect on its lattice (0, 25, 52, 73 and 95% RH). Very slight shifting of the 0% RH peaks at about 7.7, 18.3, 18.5, 20.5, 20.8° in 2θ is observed as the relative humidity is increased. The peaks at about 7.7, 20.8, and 24.1 also appear to become slightly broadened and less resolved at higher relative humidities, indicating that water is being sorbed into amorphous components (or plasticizes the solid), particularly at 73 and 95% RH. The shifting of peaks in the XRD patterns of F-I is less dramatic than the peak shifts observed as F-III was exposed to different relative humidities. This suggests that the F-I lattice does not undergo the same expansion and/or contraction as the F-III lattice.

F-I and F-III were found to be stable over the entire relative humidity range, despite the ability of F-III to sorb nearly twice as much water. The two forms were found to have comparable crystal size, morphology, aqueous solubilities and dissolution rates.

Figure 5:
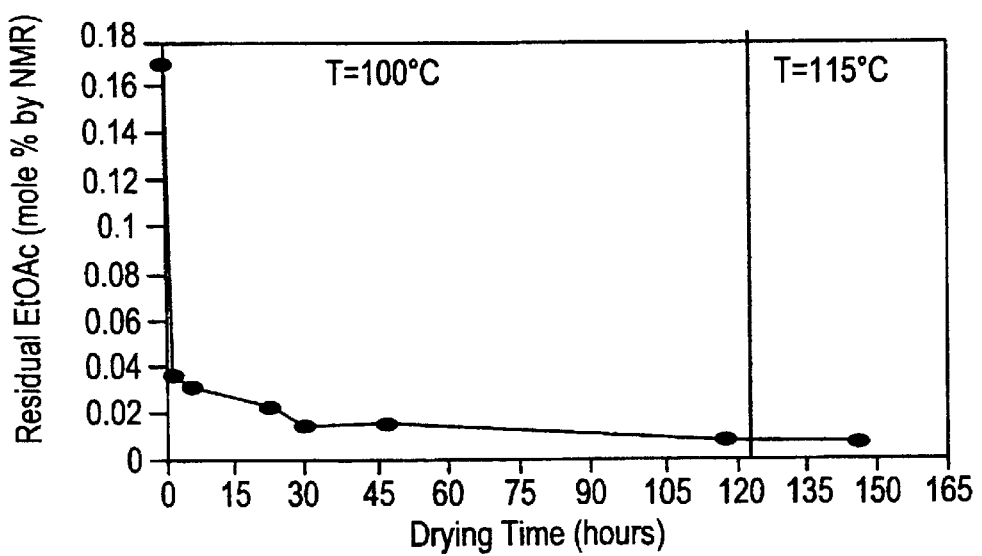
FIG. 5 depicts desolvation of S-II as a function of drying time and temperature.

A drying study was carried out to monitor the desolvation of S-II as a function of drying time and temperature (see FIG. 5). XRD patterns were taken at various timepoints during the desolvation experiment. Many diffraction peaks from the desolvation study of S-II appear at similar angles to F-I, confirming that the lattices of S-II and F-I are very similar. The disappearance of diffraction peaks at about 6.8, 7.2 and 14.0° in 2θ after only minimal drying suggests that these reflections may be attributed to crystallographic planes containing partial electron density of ethyl acetate molecules.

Extended annealing of the solvated material under vacuum at high temperatures yielded F-I. F-I prepared this way showed a high degree of crystallinity by XRD. Therefore, material generated by crystallization from a solution of ethanol and ethyl acetate followed by vacuum drying for only a few hours as taught in '474 showed very poor crystallinity because such a procedure results in partially desolvated S-II.

F-I and F-III have several advantages over the prior art form of arzoxifene described above. Relative to the arzoxifene produced by the procedures taught in '474, F-I and F-III are more stable at ambient temperature and are, therefore, more amenable to pharmaceutical development, i.e., development of a dosage formulation. In addition, F-I and F-III are much more crystalline than the form disclosed in '474. Crystalline materials are generally less hygroscopic and more stable (e.g., less prone to chemical degradation, maintains consistent potency) than amorphous materials and are, therefore, more desirable for formulation processing. Furthermore, unlike the form of arzoxifene produced by the procedures taught in '474, which contained ethyl acetate and water in its lattice, F-I and F-III contain only water.

Characterization Methods

DSC measurements were performed on a TA Instruments 2920 Modulated DSC attached to a Thermal Analyst 3100 and equipped with a refrigerated cooling system. Samples (3–5 mg) were heated in crimped aluminum pans from 10 to 240° C. at a heating rate of 2° C./min.

TGA analyses were performed on a TA Instruments 2050 Thermogravimetric Analyzer attached to a Thermal Analyst 3100. Samples (5–10 mg) were heated in open pans from 25° C. to 250° C. at a heating rate of 5° C./min.

XRD patterns were obtained on a Siemens D5000 X-ray powder diffractometer, equipped with a CuK$\alpha$ source ($\lambda$=1.54056 Å) and a Kevex solid-state detector, operating at 50 kV and 40 mA. Each sample was scanned between 4° and 35° in 2$\theta$. Samples were allowed to equilibrate for at least 30 minutes at the desired temperature and/or relative humidity before data collection.

Hygroscopicity measurements were made for F-I and F-III using the VTI method as follows. Each sample was dried under vacuum at 60° C. until no further weight loss was detected, at which time the sample chamber was brought to 0% relative humidity. Moisture sorption isotherms were obtained at 25° C. using a VTI vacuum moisture balance with the following conditions: sample size 10–15 mg, adsorption/desorption range 0–95% relative humidity, step interval 5%, sample interval 10 minutes.

The following examples further illustrate processes for preparing the hydrate of the present invention. The examples are not intended to be limiting to the scope of these processes in any respect, and should not be so construed.

EXAMPLE

Example 1

F-III From 6-Isopropoxy-3-(4-[2-(piperidin-1-yl) ethoxy]phenoxy)-2-(4-methoxyphenyl)benzo[b] thiophene Hydrochloride To a methylene chloride solution (100 mL) of 6-isopropoxy-3-(4-[2-(piperidin-1-yl)ethoxy]phenoxy)-2-(4-methoxyphenyl)benzo[b]thiophene hydrochloride (10 g, 18 mmol) under a nitrogen atmosphere at −10° C. to −20° C., was added BCl$_{3(g)}$ (4.23 g, 34 mmol) at a rate which maintains the temperature of the reaction below −10° C. After the addition was complete, the reaction was allowed to stir for an additional 2 hours. To the reaction, isopropyl alcohol (IPA, 12.35 mL, 167 mmol) was slowly added at less than −10° C. and stirring was continued for 30 minutes. A separate flask was charged with 100 mL water and cooled with an ice bath to approximately 0° C. The product solution was transferred to the water via cannula, maintaining vigorous stirring. The resultant white slurry was allowed to stir at 0° C. for 1 hour. The product was recovered by filtration and rinsed with 25 mL 40% CH$_2$Cl$_2$/water then with 25 mL cold water. The product was suspended into 60 mL IPA and 60 mL water and heated to 60° C. A solution was obtained at 48° C. Additional water (120 mL) was added. The solution was allowed to cool to 35° C. and the slurry was further cooled slowly to 0–5° C. and stirred for several hours. The product was isolated by filtration and washed with cold deionized water (25 mL). F-III wetcake was dried to a constant weight in vacuo at 50° C. for 12 to 24 hours to provide F-III.

Example 2

F-III From 6-Benzyloxy-3-(4-[2-(piperidin-1-yl) ethoxy]phenoxy)-2-(4-methoxyphenyl)benzo[b] thiophene-(S-oxide)

To a 250 mL Parr bottle was added deionized water (5.25 mL), 1M HCl (7.74 mL, 7.75 mmol), 10% Pd/C (type A32110, 1.37 g, 1.29 mmol Pd), [6-benzyloxy-3-(4-[2-(piperidin-1-yl)ethoxy]phenoxy)-2-(4-methoxyphenyl) benzo[b]thiophene-(S-oxide) (3 g, 5.16 mmol), and isopropyl alcohol (32 mL) at ambient temperature. The bottle was fitted to a Parr shaker, sequentially evacuated and gassed with nitrogen twice, and subsequently evacuated and filled with hydrogen gas to a pressure of 30 psig. The shaker was started and the reaction mixture was heated to 60° C. The reaction was determined to be complete by HPLC analysis after approximately 4 hours. The reaction mixture was filtered through a pad of diatomaceous earth, and the pad was washed with 0.1 M HCl (2×10 mL). The solvent was removed in vacuo at approximately 50° C. The resultant residue was dissolved into 50% isopropyl alcohol/deionized water (30 mL) and gently heated on a steam bath until a solution was obtained. To the solution was added deionized water (22 mL) and the solution was allowed to cool to ambient temperature. The product slurry is further cooled to 0° C. The product was isolated by filtration, washed with cold deionized water (2×15 mL), and dried in vacuo at 50° C. to constant weight to provide F-III.

Example 3

F-III from [6-Isopropoxy-3-[4-[2-(piperidin-1-yl) ethoxy)phenoxy]-2-(4-methoxyphenyl]benzo[b] thiopene-(S-oxide)

Methylene chloride (105 L) and [6-isopropoxy-3-[4-[2-(piperidin-1-yl)ethoxy)phenoxy]-2-(4-methoxyphenyl)] benzo[b]thiopene-(S-oxide) (10.5 kg) are combined and cooled to −15 to −20° C. Boron trichloride (4.6 kg) is added while maintaining the reaction temperature between −10 and −20° C. Stirring is continued until the area % by HPLC of the starting material is less than 1%. HPLC system (4.6 mm ID×25 cm Zorbax SB-Phenyl column 30° C., 70:30 methanol: 0.01 N sulfuric acid; flow 1.5 ml/min; detector 300 nm). Isopropanol (10.28 kg) is added while maintaining the reaction temperature between −10 and −20° C. The reaction mixture is stirred for 30 to 45 minutes. The crude reaction product is isolated by adding the reaction mixture to an additional 105 L of water, pre-cooled to 2 to 7° C. while maintaining the reaction temperature at 2 to 7° C. The addition is followed by a methylene chloride rinse (20 L) pre-cooled to 7 to 2° C. The crystalline slurry is stirred for 2 to 3 hours and filtered and sequentially washed with methylene chloride (26 kg) pre-cooled to 7 to 2° C. and water (53 L) pre-cooled to 7 to 2° C. The crude wet cake is combined with water (42 L) and isopropanol (40 L) and heated to 65 to 70° C. to effect dissolution. The hot solution is filtered. The filtration is followed with a rinse consisting of a mixture of isopropanol (20 L) and water (21 L) heated to 65 to 70° C. and a rinse consisting of water (126 L) pre-heated to 65 to 70° C. The solution is cooled to 40 to 45° C., seeded and stirred at this temperature for 2 to 3 hours to allow crystal growth. The slurry is cooled to 0 to 5° C., stirred for 3 to 4 hours and filtered. The filter cake is washed with water (122.6L) pre-cooled to 2 to 7° C. The product is vacuum dried at a maximum temperature of 50° C. until the change in cake weight was less than 0.05 kgs over a 2–4 hour period. Yield: 8.468 kgs (87.3%). HPLC potency: 98.5%. Water by Karl Fischer: 3.0%. Total related substances by HPLC: 1.79%.

Example 4

F-III from [6-Benzyloxy-3-[4-[2-(piperidin-1-yl) ethoxy)phenoxy]-2-(4-methoxyphenyl)]benzo[b] thiopene-(S-oxide)

Tetrahydrofuran (261 ml), water (45 ml) concentrated sulfuric acid (6.14 g) and [6-benzyloxy-3-[4-[2-(piperidin-1-yl) ethoxy)phenoxy]-2-(4-methoxyphenyl)]benzo[b] thiopene-(S-oxide) (HPLC potency 99%, HPLC total related substance level 0.35%) were combined and stirred until homogeneous. 10% Pd/C (5.6 g slurried in 22 ml of water) was added with a 5 ml water rinse. The resulting slurry was evacuated and overlaid with 60 psi of hydrogen. The reaction temperature was adjusted to 30° C. After 2 hours, 10% Pd/C (5.6 g) of was added with water (30 ml). Hydrogenation at 60 psi and 30° C. was continued for an additional 22 hours. An additional 4.40 g of 10% Pd/C in 30 ml water was added and hydrogenation at 60 psi and 30° C. continued for an additional 2.5 hours. The catalyst was removed by filtration and the pH of the filtrate was adjusted to 7.24 with 50% sodium hydroxide. Sodium chloride (8.66 g) dissolved in water (18 ml) was added and the biphasic solution stirred for 30 minutes. The phases were separated and the aqueous phase was back extracted with 50 ml of tetrahydrofuran. The organic phases were combined and concentrated by atmospheric distillation to a volume of 50 ml. To the concentrate at 24° C. was added methanol, 180 ml over a 1 hour period. The resulting crystalline slurry was stirred for 30 minutes at 24° C., cooled to 0° C. and stirred for 1 hour. The solids were isolated by filtration and washed sequentially with 39 ml of water and 39 ml of methanol followed by vacuum drying overnight at 50° C. Yield 15.52 g (67.8%)

Isopropanol (33 ml), water (66 ml) and 10 g of solid isolated from above were combined. To the stirred mixture at 25° C. is added 1.8 M HCl (21 ml). The solids quickly dissolved followed by re-precipitation of the hydrochloride salt. After stirring for 30 minutes, the slurry was heated to 70° C. to effect dissolution of all of the solids. The solution was cooled to 60° C. and 33 ml of water added. The resulting solution was cooled to 25° C. over a 3 hour period during which time the hydrochloride salt precipitated. The slurry was stirred for approximately 3 hours at 25° C., filtered, washed with water (30 ml) and vacuum dried overnight at 50° C. to yield 8.9 g (82.7%) of F-III. HPLC potency: 96.5%. Water by Karl Fischer: 2.44%. HPLC related substances: 1.09%.

Utilities

As used herein, the term "effective amount" means an amount of F-III that is capable of inhibiting conditions, or detrimental effects thereof, described herein. When F-III is co-administered with estrogen, progestin, an aromatase inhibitor, an LHRH analogue, or an AChE inhibitor, the term "effective amount" also means an amount of such an agent capable of producing its intended effect.

The terms "inhibiting" and "inhibit" include their generally accepted meaning, i.e., preventing, prohibiting, restraining, alleviating, ameliorating, slowing, stopping, or reversing the progression or severity of a pathological condition, or sequela thereof, described herein.

The terms "preventing", "prevention of", "prophylaxis", "prophylactic" and "prevent" are used herein interchangeably and refer to reducing the likelihood that the recipient of F-III will incur or develop any of the pathological conditions, or sequela thereof, described herein.

The terms "estrogen deprived" and "estrogen deprivation" refer to a condition, either naturally occurring or clinically induced, where a woman can not produce sufficient endogenous estrogenic hormones to maintain estrogen dependent functions, e.g., menses, homeostasis of bone mass, neuronal function, cardiovascular condition, etc. Such estrogen deprived situations arise from, but are not limited to, menopause and surgical or chemical ovarectomy, including its functional equivalent, e.g., medication with an aromatase inhibitor, GnRH agonists or antagonists, ICI 182780, and the like. Disease states associated with an estrogen deprived state include, but are not limited to: bone loss, osteoporosis, cardiovascular disease and hyperlipidemia.

As used herein, the term "estrogen" includes steroidal compounds having estrogenic activity such as, for example, 17β-estradiol, estrone, conjugated estrogen (Premarin®), equine estrogen 17β-ethynyl estradiol, and the like. A preferred estrogen-based compound is Premarin®, and norethylnodrel.

As used herein, the term "progestin" includes compounds having progestational activity such as, for example, progesterone, norethylnodrel, nongestrel, megestrol acetate, norethindrone, and the like. Norethindrone is a preferred progestin-based agent.

As used herein the term "aromatase inhibitor" includes compounds capable of inhibiting aromatase, for example commercially available inhibitors such as aminoglutemide (CYTANDREN®), Anastrazole (ARIMIDEX®), Letrozole (FEMARA®), Formestane (LENATRON®), Exemestane (AROMASIN®), and the like.

As used herein, the term "LHRH analogue" refers to an analogue of lutenizing hormone releasing hormone that inhibits estrogen production in a premenopausal women including for example, goserlin (ZOLADEX®), leuprolide (LUPRON®) and the like.

As used herein, the term "AChE inhibitor" includes compounds that inhibit acetyl choline esterase, for example, physostigmine salicylate, tacrine hydrochloride, donepezil hydrochloride and the like.

The term "up-regulate ChAT" refers to increasing the enzymatic activity of ChAT, i.e., promoting the conversion of choline to acetyl choline. This promotion would include an increase in the efficiency and/or rate of reaction of ChAT and choline and/or an increase in the amount of ChAT present at the site of action. This increase in the amount of enzyme present may be due to gene regulation or other synthetic step of the enzyme's formation and/or a decrease in the enzyme's de-activation and metabolism.

Selected Testing Procedures

General Rat Preparation Procedure: Seventy-five day old (unless otherwise indicated) female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room was 12 hours light and 12 hours dark.

Dosing Regimen Tissue Collection: After a one week acclimation period (therefore, two weeks post-OVX) daily dosing with F-III is initiated. 17α-ethynyl estradiol or F-III is given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine:Xylazine (2:1, v:v) mixture and a blood sample is collected by cardiac puncture. The animals are then sacrificed by asphyxiation with $CO_2$, the uterus is removed through a midline incision, and a wet uterine weight is determined. 17α-ethynyl estradiol is obtained from Sigma Chemical Co., St. Louis, Mo.

Cardiovascular Disease/Hyperlipidemia

The blood samples from above are allowed to clot at room temperature for 2 hours, and serum is obtained following centrifugation for 10 minutes at 3000 rpm. Serum cholesterol is determined using a Boehringer Mannheim Diagnostics high performance cholesterol assay. Briefly the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay

The uteri from above are kept at 4° C. until time of enzymatic analysis. The uteri are then homogenized in 50 volumes of 50 mM Tris buffer (pH–8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosonophils in the uterus is an indication of estrogenic activity of a compound. The maximal velocity of a 15 second interval is determined over the initial, linear portion of the reaction curve.

Inhibition of Bone Loss (Osteoporosis) Test Procedure

Following the general preparation procedure described above, the rats are treated daily for thirty-five days (6 rats per treatment group) and sacrificed by carbon dioxide asphyxiation on the 36th day. The thirty-five day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized X-rays generated and analyzed by an image analysis program (NIH image) at the distal metaphysis. The proximal aspect of the tibiae from these animals are also scanned by quantitative computed tomography. In accordance with the above procedures, F-III or ethynyl estradiol ($EE_2$) in 20% hydroxypropyl β-cyclodextrin are orally administered to test animals. F-III is also useful in combination with estrogen or progestin.

MCF-7 Proliferation Assay

MCF-7 breast adenocarcinoma cells (ATCC HTB 22) are maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells are switched to maintenance medium supplemented with 10% dextran coated charcoal stripped fetal bovine serum (DCC-FBS) assay medium) in place of 10% FBS to deplete internal stores of steroids. MCF-7 cells are removed from maintenance flasks using cell dissociation medium ($Ca++/Mg++$ free HBSS (phenol red-free) supplemented with 10 mM HEPES and 2 mM EDTA). Cells are washed twice with assay medium and adjusted to 80,000 cells/mL. Approximately 100 mL (8,000 cells) are added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control are prepared in assay medium and 50 mL transferred to triplicate microcultures followed by 50 mL assay medium for a final volume of 200 mL. After an additional 48 hours at 37° C. in a 5% $CO_2$ humidified incubator, microcultures are pulsed with tritiated thymidine (1 uCi/well) for 4 hours. Cultures are terminated by freezing at –70° C. for 24 hours followed by thawing and harvesting of microcultures using a Skatron Semiautomatic Cell Harvester. Samples are counted by liquid scintillation using a Wallac BetaPlace β counter.

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

F-III is administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

Uterine Fibrosis Test Procedures

Test 1: Between 3 and 20 women having uterine fibrosis are administered F-III. The amount of compound administered is from 0.1 to 1000 mg/day, and the period of administration is 3 months. The women are observed during the period of administration, and up to 3 months after discontinuance of administration, for effects on uterine fibrosis.

Test 2: The same procedure is used as in Test 1, except the period of administration is 6 months.

Test 3: The same procedure is used as in Test 1, except the period of administration is 1 year.

Test 4: Prolonged estrogen stimulation is used to induce leiomyomata in sexually mature female guinea pigs. Animals are dosed with estradiol 3–5 times per week by injection for 2–4 months or until tumors arise. Treatment consisting of F-III or vehicle is administered daily for 3–16 weeks and then animals are sacrificed and the uteri harvested and analyzed for tumor regression.

Test 5: Tissue from human leiomyomas are implanted into the peritoneal cavity and/or uterine myometrium of sexually mature, castrated, female, nude mice. Exogenous estrogen is supplied to induce growth of the explanted tissue. In some cases, the harvested tumor cells are cultured in vitro prior to implantation. Treatment consisting of F-III or vehicle is supplied by gastric lavage on a daily basis for 3–16 weeks and implants are removed and measured for growth or regression. At the time of sacrifice, the uteri are harvested to assess the status of the organ.

Test 6: Tissue from human uterine fibroid tumors is harvested and maintained, in vitro, as primary non-transformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, F-III, and vehicle. Levels of steroid hormone receptors are assessed weekly to determine whether important cell characteristics are maintained in vitro. Tissue from 5–25 patients is utilized.

Test 7: F-III's ability to inhibit estrogen-stimulated proliferation of leiomyoma-derived ELT cell lines is measured substantially as described in Fuchs-Young, et al., "Inhibition of Estrogen-Stimulated Growth of Uterine Leiomyomas by Selective Estrogen Receptor Modulators", Mol. Car., 17(3): 151–159 (1996), the teachings of which are herein incorporated by reference.

Endometriosis Test Procedures

Test 1: Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed. On the day following surgery, animals in Groups 1 and 2 receive intraperitoneal injections of water for 14 days whereas animals in Group 3 receive intraperitoneal injections of 1.0 mg of F-III per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Test 2: Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. Approximately 50 days following surgery, animals assigned to Group 1 receive intraperitoneal injections of water for 21 days whereas animals in Group 2 receive intraperitoneal injections of 1.0 mg of F-III per kilogram of body weight for the same duration. Following 21 days of treatment, each female is sacrificed and the endometrial explants and adrenals are removed and weighed. The explants are measured as an indication of growth. Estrous cycles are monitored.

Test 3: Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

Test 4: Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of F-III supplied by gastric lavage on a daily basis for 3–16 weeks, and implants are removed and measured for growth or regression. At the time of sacrifice, the uteri are harvested to assess the status of the intact endometrium.

Test 5: Tissue from human endometrial lesions is harvested and maintained in vitro as primary non-transformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, F-III, and vehicle. Levels of steroid hormone receptors are assessed weekly to determine whether important cell characteristics are maintained in vitro. Tissue from 5–25 patients is utilized.

CNS Disorders Including Alzheimer's Disease

Estrogens, such. as 17β-estradiol, regulate gene transcription by binding to estrogen receptors (ER) which reside in the cytoplasm of certain cell populations. Ligand activation of the ER is a prerequisite for nuclear transport of the complex where binding to a 13 base-pair palindromic DNA consensus sequence (estrogen response element, or ERE) begins assembly of a transcriptional apparatus which culminates in the activation of appropriate target genes. A variety of genes have been identified which are regulated by estrogen. These include cytoskeletal proteins, neurotransmitter biosynthetic and metabolic enzymes and receptors, as well as other hormones and neuropeptides. ERE's have been identified in many estrogen-responsive genes including vitellogenin, c-fos, prolactin, and lutenizing hormone.

Of significance in the central nervous system, ERE-like sequences have been identified in $p75^{ngr}$ and trkA, both of which serve as signaling molecules for the neurotrophins: nerve growth factor (NGF), brain derived nerve growth factor (BDNGF), and neurotrophin-3.

BDNF as well as NGF have been shown to promote the survival of cholinergic neurons in culture. It is postulated that if the interactions between neurotrophins and estrogens are important for the development and survival of basal forebrain neurons (which degenerate in Alzheimer's disease) then clinical conditions in which an estrogen deficiency exists (as after menopause) may contribute to a loss of these neurons.

The following experiment is conducted in ovariectomized rats (prepared as described above) to determine the similarities and/or differences between F-III and estrogen at affecting gene expression in various brain regions. Six week old rats are dosed daily with subcutaneous injections of estradiol benzoate (0.03 mg/kg), F-III or vehicle (control). After five weeks of treatment, animals are sacrificed and their brains removed and hippocampi collected by microdissection. The hippocampi are fast frozen in liquid nitrogen and stored at −70° C. Total RNA is prepared from pooled tissue from the appropriate treatment and control groups and reverse transcribed using a 3' oligonucleotide primer which is selected for specific MRNA (poly–A+) populations. Polymerase chain reactions (PCR) are carried out in a cocktail consisting of: random 5' oligonucleotides (10 base-pairs in length; total of 150), reaction buffer, Taq polymerase, and a $^{32}$PdTCP.

After 40 rounds of amplification, the reaction products are size fractionated on a 6% TBE-urea gel, dried and exposed to X-ray film. The resulting mRNA display patterns are compared between treatment groups.

Use of F-III in Conjunction with Estrogen

Peri- and post-menopausal women often undergo hormone replacement therapy (HRT) to combat negative consequences associated with the drop in circulating endogenous estrogen, e.g., to treat hot flashes. However, HRT has been associated with increased risks of certain cancers including uterine and breast cancer. F-III may be employed in conjunction with HRT to inhibit these risks.

Use of F-III in Conjunction With an Aromatase Inhibitor

By definition, the ovaries of a postmenopausal woman are not functioning. Her only source of estrogen is through conversion of adrenal androgens to estrogens by the enzyme aromatase, which is found in peripheral tissues (including fat, muscle and the breast tumor itself). Thus, drugs that inhibit aromatase (aromatase inhibitors) deplete the postmenopausal woman of circulating estrogen. Estrogen deprivation by means of aromatase inhibition is an important treatment option for patients with metastatic breast cancer. During therapy with an aromatase inhibitor, lack of circulating estrogen may cause negative, unintended side-effects, for example on serum lipid levels. F-III may be employed to inhibit these negative effects.

Use of F-III in Conjunction with a LHRH Analogue

Continuous exposure to a LHRH (lutenizing hormone releasing hormone) analogue inhibits estrogen production in the premenopausal women by desensitizing the pituitary gland, which then no longer stimulates the ovaries to produce estrogen. The clinical effect is a "medical oophrectomy" which is reversible upon cessation of the LHRH analogue. During therapy with a LHRH analogue, lack of circulating estrogen may cause negative, unintended side-effects, for example on serum lipid levels. F-III may be employed to inhibit these negative effects.

Increasing Levels of Acetyl Choline

It is known that patients suffering from Alzheimer's disease have a markedly smaller level of cholinergic neurons in the hippocampus than their non-Alzheimer peers. The progressive loss of these cholinergic neurons appears to mirror the progressive loss in memory and cognitive function in these patients. It is thought that one reason for the decline of these neurons is the loss or decreased function of the neurotransmitter, acetyl choline.

The level of acetylcholine in a neuron is basically determined by where the equilibrium between its bio-synthesis and bio-degradation lies. The enzyme choline acetyltransferase (ChAT) is primarily responsible for its synthesis and acetylcholineesterase (AChE) for its degradation.

In the order to determine F-III's effect on levels of ChAT, the following experiment is performed: Following the general rat preparation procedure described above, 40 rats are dosed daily by subcutaneous injection or oral gavage with F-III at 3 mg/kg/day in a vehicle containing 10% cyclodextrin, estradiol benzoate at 0.03 or 0.3 mg/kg/day, or vehicle control. Animals are treated for 3 or 10 days. There are twenty animals per each dosing regimen. At the appropriate time intervals, the animals are sacrificed and their brains dissected. The particular portions of the brains are homogenized and assayed. Homogenates from the hippocampus and frontal cortex were processed and determination of ChAT activity is made by a radio-labelled assay of the bio-synthesis of acetyl choline. This procedure may be found in Schoepp et al., *J. Neural Transmiss.*, 78:183–193, 1989, the teachings of which are incorporated by reference.

As expected, in the OVX animals, ChAT levels are reduced >50% (p<0.001) compared to the sham operated controls.

In another embodiment of the present invention, F-III is used in combination with an AChE inhibitor. Use of an AChE inhibitor increases levels of acetylcholine by blocking its degradation via inhibition of AChE.

Benign Prostatic Hyperplasia (BPH)

For background on the link between estrogen action and treatment of BPH and prostate carcinoma, see PCT Application No. WO 98/07274, International Publication Date: Oct. 15, 1998.

In the experiments described below, the ability of F-III to bind at estrogen receptors in several human prostatic cancer cell lines is evaluated.

Lysates of the LNCaP, DU-45 and PC-3 human prostatic cancer cell lines are prepared in a TEG medium comprising 50 nM Tris·HCl pH 7.4, 1.5 mM ethylenediamine tetraacetic acid (EDTA) 0.4 M KCl, 10% glycerol, 0.5 mM 2-ME, and 10 mM sodium molybdate further containing the protease inhibitors pepstatin (1 mg/mL), leupeptin (2 mg/mL), aprotinin (5 mg/mL) and phenylmethylsulfonyl fluoride (PMSF, 0.1 mM) (TEGP).

The cell lysates are centrifuged and the pellets resuspended in cold TEGP (1 mL TEGP/100 mg of pellet) and sonicated for 30 seconds (duty cycle 70%, output 1.8) on a Branson Model 450 Sonifier. Lysates are pelleted by centrifugation at 10,000×G for 15 minutes at 4° C. after which the supernates are withdrawn and either used immediately or stored at −70° C.

Competitive Binding Assay: The binding buffer is TEG in which the 0.4 M KCl is replaced by 50 mM NaCl and to which 1 mg/mL of ovalbumin had been further added (TEGO). F-III is diluted to 20 nM in TEGO from which 3-fold serial dilutions are prepared. Assays are performed in round-bottom polyprolylene microplates in triplicate microwells. Each well receives 35 mL of tritiated 17β-estradiol (0.5 nM, specific activity 60.1 Ci/mmol, DuPont-New England Nuclear, Boston, Mass.) and 35 mL of cold competitot test compound (0.1 nM–5 mM) or TEGO, and following incubation for 5 minutes at 4° C. with shaking, 70 mL of MCF-7 cell line lysate.

Plates are incubated for 24 hours at 4° C. after which time 70 mL of dextran-coated charcoal (DCC) is added to each well followed by vigorous shaking for 8 minutes at 4° C. The plates are then centrifuged at 1500×G for 10 minutes at 4° C. Supernate is harvested from each well into a flexible polystyrene microplate for scintillation counting in a Wallac Micobeta Model 1450 counter. Radioactivity is expressed as disintegrations per minute (DPM) after correcting for counting efficiency (35–40%) and background. Additional controls are total counts and total counts+DCC to defined the lower limit of DCC extractable counts. The results of these competitive binding assays are expressed as mean percent bound (% Bound) +/− standard deviation using the formula:

$$\% \text{ Bound} = \frac{DPM_{test\ compound} - DPM_{total\ count\ +DCC}}{DPM_{no\ test\ compound} - DPM_{total\ count\ +DCC}} \times 100$$

Prevention of Breast Cancer

This invention also relates to the administration of F-III to a recipient who is at risk of developing de novo breast cancer. The term "de novo", as used herein, means the lack of transformation or metamorphosis of normal breast cells to cancerous or malignant cells in the first instance. Such a transformation may occur in stages in the same or daughter cells via an evolutionary process or may occur in a single, pivotal event. This de novo process is in contrast to the metastasis, colonization, or spreading of already transformed or malignant cells from the primary tumor site to new locations.

A person who is at no particular risk of developing breast cancer is one who may develop de novo breast cancer, has no evidence or suspicion of the potential of the disease above normal risk, and who has never had a diagnosis of having the disease. The greatest risk factor contributing to the development of breast carcinoma is a personal history of suffering from the disease, or an earlier occurrence of the disease, even if it is in remission with no evidence of its presence. Another risk factor is family history of the disease.

Induction of mammary tumors in rats by administration of the carcinogen N-nitroso-N-methylurea is a well-accepted animal model for the study of breast cancer and has been found suitable for analyzing the effect of chemopreventive agents.

In two separate studies, 55-day old female Sprague-Dawley rats are given an intravenous (Study 1) or intraperitoneal (Study 2) dose of 50 mg of N-nitroso-N-methylurea per kilogram of body weight one week prior to feeding ad libitum a diet into which varying amounts of F-III, (Z)-2-[4-(1,2-diphenyl-1-butenyl)phenoxy]-N,N-dimethylethanamine base (tamoxifen base), or control are blended.

In Study 1, the dietary doses of 60 mg/kg of diet and 20 mg/kg of diet translates into roughly comparable doses of 3 and 1 mg/kg of body weight for the test animals.

In Study 2, the dietary doses of 20, 6, 2, and 0.6 mg/kg of diet translates roughly into comparable doses of 1, 0.3, 0.1 and 0.03 mg/kg of body weight for the test animals.

Rats are observed for evidence of toxicity and are weighed and palpated for tumor formation once a week. The animals are sacrificed after thirteen weeks (Study 1) or eighteen weeks (Study 2) and tumors are confirmed and weighed at autopsy.

Formulations

The term "pharmaceutical" when used herein as an adjective means substantially non-deleterious to the recipient mammal. By "pharmaceutical formulation" it is meant the carrier, diluent, excipients and active ingredient(s) must be compatible with the other ingredients of the formulation, and not deleterious to the recipient thereof.

F-III is preferably formulated prior to administration. The selection of the formulation should be decided by the attending physician taking into considerations the same factors involved with determining the effective amount.

The total active ingredients in such formulations comprises from 0.1% to 99.9% by weight of the formulation. Preferably, no more than two active ingredients are contained in said formulation. That is, it is preferred to formulate F-III with a second active ingredient selected from an estrogen, progestin, aromatase inhibitor, LHRH analogue and AChE inhibitor. Most preferred formulations are those where F-III is the sole active ingredient.

Pharmaceutical formulations of the present invention are prepared by procedures known in the art using well known and readily available ingredients. For example, F-III, either alone, or in combination with an estrogen, progestin, aromatase inhibitor, LHRH analogue, or an AChE inhibitor compound, are formulated with common excipients, diluents, or carriers, and formed into tablets, capsules, suspensions, solutions, injectables, aerosols, powders, and the like.

Pharmaceutical compositions of this invention for parenteral administration comprise sterile aqueous or non-aqueous solutions, dispersions, suspensions, or emulsions, as well as sterile powders which are reconstituted immediately prior to use into sterile solutions or suspensions. Examples of suitable sterile aqueous and non-aqueous carriers, diluents, solvents or vehicles include water, physiological saline solution, ethanol, polyols (such as glycerol, propylene glycol, poly(ethylene glycol), and the like), and suitable mixtures thereof, vegetable oils (such as olive oil), and injectable organic esters such as ethyl oleate. Proper fluidity is maintained, for example, by the use of coating materials such as lecithin, by the maintenance of proper particle size in the case of dispersions and suspensions, and by the use of surfactants.

Parenteral compositions may also contain adjuvants such as preservatives, wetting agents, emulsifying agents, and dispersing agents. Prevention of the action of microorganisms is ensured by the inclusion of antibacterial and antifungal agents, for example, paraben, chlorobutanol, phenol sorbic acid, and the like. It may also be desirable to include isotonic agents such as sugars, sodium chloride, and the like. Prolonged absorption of injectable formulations may be brought about by the inclusion of agents which delay absorption such as aluminum monostearate and gelatin.

In some cases, in order to prolong the effect of the drug, it is desirable to slow the absorption of the drug following subcutaneous or intramuscular injection. This may be accomplished by the use of a liquid suspension of crystalline material of low water solubility or by dissolving or suspending the drug in an oil vehicle. In the case of the subcutaneous or intramuscular injection of a suspension containing a form of the drug with low water solubility, the rate of absorption of the drug depends upon its rate of dissolution.

Injectable "depot" formulations of F-III are made by forming microencapsulated matrices of the drug in biodegradable polymers such as poly(lactic acid), poly(glycolic acid), copolymers of lactic and glycolic acid, poly (orthoesters), and poly (anhydrides) these materials which are described in the art. Depending upon the ratio of drug to polymer and the characteristics of the particular polymer employed, the rate of drug release can be controlled.

Injectable formulations are sterilized, for example, by filtration through bacterial-retaining filters, or by presterilization of the components of the mixture prior to their admixture, either at the time of manufacture or just prior to administration (as in the example of a dual chamber syringe package).

Solid dosage forms for oral administration include capsules, tablets, pills, powders, and granules. In such solid dosage forms, F-III is mixed with at least one inert, pharmaceutical carrier such as sodium citrate, or dicalcium phosphate, and/or (a) fillers or extenders such as starches, sugars including lactose and glucose, mannitol, and silicic acid, (b) binding agents such as carboxymethyl-cellulose and other cellulose derivatives, alginates, gelatin, poly (vinylpyrrolidine), sucrose and acacia, (c) humectants such as glycerol, (d) disintegrating agents such as agar-agar, calcium carbonate, sodium bicarbonate, potato or tapioca starch, alginic acid, silicates and sodium carbonate, (e) moisturizing agents such as glycerol; (f) solution retarding agents such as paraffin, (g) absorption accelerating agents such as quaternary ammonium compounds, (h) wetting agents such as cetyl alcohol and glycerin monostearate, (i) absorbents such as kaolin and bentonite clay, and (j) lubricants such as talc, calcium stearate, magnesium stearate, solid poly(ethylene glycols), sodium lauryl sulfate, and mixtures thereof. In the case of capsules, tablets and pills, the dosage form may also contain buffering agents.

Solid compositions of a similar type may also comprise the fill in soft or hard gelatin capsules using excipients such as lactose as well as high molecular weight poly(ethylene glycols) and the like.

Solid dosage forms such as tablets, dragees, capsules, pills and granules can also be prepared with coatings or shells such as enteric coatings or other coatings well known in the pharmaceutical formulating art. The coatings may contain opacifying agents or agents which release the active ingredient(s) in a particular part of the digestive tract, as for example, acid soluble coatings for release of the active ingredient(s) in the stomach, or base soluble coatings for release of the active ingredient(s) in the intestinal tract.

The active ingredient(s) may also be microencapsulated in a sustained-release coating, with the microcapsules being made part of a pill of capsule formulation.

Liquid dosage forms for oral administration of F-III include solution, emulsions, suspensions, syrups and elixirs. In addition to the active components, liquid formulations may include inert diluents commonly used in the art such as water or other pharmaceutical solvents, solubilizing agents and emulsifiers such as ethanol, isopropanol, ethyl carbonate, ethyl acetate, benzyl alcohol, benzyl benzoate, propylene glycol, 1,3-butylene glycol, dimethyl formamide, oils (in particular, cottonseed, ground nut, corn, germ, olive, castor, and sesame oils), glycerol, tetrahydrofurfuryl alcohol, poly(ethylene glycols), fatty acid esters of sorbitol, and mixtures thereof.

Besides inert diluents, the liquid oral formulations may also include adjuvants such as wetting agents, emulsifying and suspending agents, and sweetening, flavoring, and perfuming agents.

Liquid suspension, in addition to the active ingredient(s) may contain suspending agents such as ethoxylated isostearyl alcohols, polyoxyethylene sorbitol and sorbitan esters, microcrystalline cellulose, aluminum metahydroxide, bentonite clay, agar-agar, and tragacanth, and mixtures thereof.

Compositions for rectal or intravaginal administration are prepared by mixing F-III with suitable non-irritating excipients such as cocoa butter, polyethylene glycol or any suppository wax which is a solid at room temperature, but liquid at body temperature and therefore melt in the rectum or vaginal cavity to release the active component(s). The compounds are dissolved in the melted wax, formed into the desired shape, and allowed to harden into the finished suppository formulation.

F-III may also be administered in the form of liposomes. As is know in the art, liposomes are generally derived from phospholipids or other lipid substances. Lipososome formulations are formed by mono- or multilamellar hydrated liquid crystals which are dispersed in an aqueous medium. Any non-toxic, pharmaceutical, and metabolizable lipid capable of forming liposomes can be used. The present compositions in liposome form can contain, in addition to F-III, stabilizers, excipients, preservatives, and the like. The preferred lipids are phospholipids and the phosphatidyl cholines (lecithins), both natural and synthetic.

Methods for forming liposomes are know in the art as described, for example, in Prescott, Ed., *Methods in Cell Biology*, Volume XIV, Academic Press, New York, N.Y. (1976), p. 33 et seq.

The following formulation examples are illustrative only and are not intended to limit the scope of the present invention.

Formulation 1: Gelatin Capsules

Hard gelatin capsules are prepared using the following:

| Ingredient | Quantity (mg/capsule) |
|---|---|
| F-III | 0.1–1000 |
| Starch, NF | 0–650 |

-continued

Formulation 1: Gelatin Capsules

Hard gelatin capsules are prepared using the following:

| Ingredient | Quantity (mg/capsule) |
|---|---|
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2: Tablets

| Ingredient | Quantity (mg/tablet) |
|---|---|
| F-III | 2.5–1000 |
| Cellulose, microcrystalline | 200–650 |
| Silicon dioxide, fumed | 10–650 |
| Stearate acid | 5–15 |

The components are blended and compressed to form tablets.

Formulation 3: Tablets containing approximately 10 and 50 mgs, respectively, of F-III may be prepared as follows:

| Ingredient | Quantity (mg/tablet) | Quantity (mg/tablet) |
|---|---|---|
| F-III | 11.3 | 56.5 |
| Lactose Anhydrous | 176.8 | 128.2 |
| Lactose Spray Dried Special | 44.2 | 32.0 |
| Povidone | 11.0 | 13.0 |
| Polysorbate 80 | 2.5 | 2.6 |
| Crosspovidone (Inside) | 6.25 | 6.24 |
| Crosspovidone (Outside) | 6.25 | 6.5 |
| Magnesium Stearate | 1.5 | 1.7 |
| Microcrystalline Cellulose (Outside) | 0.0 | 13.0 |

The components are blended and compressed to form tablets.

Alternatively, tablets each containing 2.5–1000 mg of F-III are made up as follows:

Formulation 4: Tablets

| Ingredient | Quantity (mg/tablet) |
|---|---|
| F-III | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

F-III, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 5: Suspensions

| Ingredient | Quantity (mg/5 ml) |
|---|---|
| F-III | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 6: Aerosol

| Ingredient | Quantity (% by weight) |
|---|---|
| F-III | 0.25 |
| Ethanol | 25.75 |
| Propellant 22 (Chlorodifluoromethane) | 70.00 |

F-III is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 7: Suppositories

| Ingredient | Quantity (mg/suppository) |
|---|---|
| F-III | 250 |
| Saturated fatty acid glycerides | 2,000 |

F-III is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 8: Intravenous Solution

| Ingredient | Quantity |
|---|---|
| F-III | 25 mg |
| Isotonic saline | 1,000 mL |

The solution of the above ingredients is intravenously administered to a patient at a rate of about 1 mL per minute.

Formulation 9: Combination Capsule I

| Ingredient | Quantity (mg/capsule) |
|---|---|
| F-III | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 10: Combination Capsule II

| Ingredient | Quantity (mg/capsule) |
|---|---|
| F-III | 50 |
| Norethylnodrel | 5 |
| Avicel pH 101 | 82.50 |
| Starch 1500 | 90 |
| Silicon Oil | 2 |
| Tween 80 | 0.50 |

Formulation 11: Combination Tablet

| Ingredient | Quantity (mg/capsule) |
|---|---|
| F-III | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

Dosage

The specific dose of F-III administered according to this invention is determined by the particular circumstances surrounding each situation. These circumstances include, the route of administration, the prior medical history of the recipient, the pathological condition or symptom being treated, the severity of the condition/symptom being treated, and the age and sex of the recipient.

Generally, an effective minimum daily dose of F-III is about 1, 5, 10, 15, or 20 mg. Typically, an effective maximum dose is about 800, 100, 60, 50, or 40 mg. Most typically, the dose ranges between 15 mg and 60 mg. The exact dose may be determined, in accordance with the standard practice in the medical arts of "dose titrating" the recipient; that is, initially administering a low dose of the compound, and gradually increasing the does until the desired therapeutic effect is observed.

Although it may be necessary to dose titrate the recipient with respect to the combination therapies discussed above, typical doses of active ingredients other than F-III are as follows: ethynyl estrogen (0.01–0.03 mg/day), mestranol (0.05–0.15 mg/day), conjugated estrogenic hormones (e.g., Premarin®, Wyeth-Ayerst; 0.3–2.5 mg/day), medroxyprogesterone (2.5–10 mg/day), norethylnodrel (1.0–10.0 mg/day), nonethindrone (0.5–2.0 mg/day), aminoglutemide (250–1250 mg/day, preferably 250 mg four times per day), anastrazole (1–5 mg/day, preferably 1 mg once per day), letrozole (2.5–10 mg/day, preferably 2.5 mg once a day), formestane (250–1250 mg per week, preferably 250 mg twice weekly), exemestane (25–100 mg/day, preferably 25 mg once per day), goserlin (3–15 mg/three months, preferably 3.6–7.2 mg once every three months) and leuprolide (3–15 mg/month, preferably 3.75–7.5 mg once every month).

Route of administration

F-III can be administered by a variety of routes including oral, rectal, transdermal, subcutaneus, intravenous, intramuscular, and intranasal. The method of administration of each estrogen- and progestin-based agent is consistent with that which is known in the art. F-III, alone or in combination with estrogen, progestin, or an AChE inhibitor generally will be administered in a convenient formulation.

The pharmaceutical compositions of this invention may be administered to humans and other mammals (e.g., dogs, cats, horses, swine and the like) orally, rectally, intravaginally, parenterally, topically, bucally or sublingually, or nasally. The term "parenteral administration" refers herein to modes of administration which include intravenous, intramuscular, intraperitoneal, instrasternal, subcutaneous, or intraarticular injection or infusion.

Mode/Length of Administration

For the majority of the methods of the present invention, F-III is administered continuously, from 1 to 3 times daily or as often as needed to deliver an effective amount of F-III to the recipient. Cyclical therapy may especially be useful in the treatment of endometriosis or may be used acutely during painful attacks of the disease. In the case of restenosis, therapy may be limited to short (1–6 months) intervals following medical procedures such as angioplasty.

We claim:

1. Crystalline 6-hydroxy-3-(4-[2-(piperidin-1-yl)ethoxy]phenoxy)-2-(4-methoxyphenyl)benzo[b]thiophene hydrochloride hydrate (F-III) having an X-ray diffraction pattern which comprises the following peaks: 4.6±0.2, 7.8±0.2, 9.3±0.2, 14.0±0.2, 17.6±0.2, 20.8±0.2, and 24.3±0.2° in 2θ; when obtained at 25±2° C. and 35±10% relative humidity from a copper radiation source (CuKα; λ=1.54056 Å).

2. A pharmaceutical formulation comprising the crystalline compound of claim 1 and one or more pharmaceutical carriers, diluents, or excipients.

3. A pharmaceutical formulation comprising the crystalline compound of claim 1; one or more pharmaceutical carriers, diluents, or excipients; and estrogen.

4. A process for preparing a compound of claim 1 which comprises crystallizing 6-hydroxy-3-(4-[2-(piperidin-1-yl)ethoxy]phenoxy)-2-(4-methoxyphenyl)benzo[b]thiophene hydrochloride from a mixture of isopropanol and water.

* * * * *